United States Patent
Bessling et al.

(10) Patent No.: US 6,833,057 B1
(45) Date of Patent: Dec. 21, 2004

(54) PURE ETHYLENE OXIDE DISTILLATION PROCESS

(75) Inventors: Bernd Bessling, Grünstadt (DE); Hans Hasse, Kaiserslautern (DE); Jürgen Plückhan, Frankenthal (DE); Thomas Mayer, Wachenheim (DE); Heinz Auer, Neulussheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/341,921
(22) PCT Filed: Jan. 29, 1998
(86) PCT No.: PCT/EP98/00480
  § 371 (c)(1),
  (2), (4) Date: Jul. 21, 1999
(87) PCT Pub. No.: WO98/33785
  PCT Pub. Date: Aug. 6, 1998

(30) Foreign Application Priority Data

Jan. 31, 1997 (DE) .......................... 197 03 627

(51) Int. Cl.[7] .......................... B01D 3/38; C07D 301/32
(52) U.S. Cl. .............................. 203/14; 203/17; 203/92; 203/95; 203/99; 203/DIG. 19; 549/541
(58) Field of Search ........................ 203/14, 17, 91–92, 203/95–96, 99, DIG. 19; 202/158; 549/541

(56) References Cited

U.S. PATENT DOCUMENTS

| | | | |
|---|---|---|---|
| 3,265,593 A | 8/1966 | Leis et al. | 203/60 |
| 3,418,338 A | 12/1968 | Gilman et al. | 549/541 |
| 4,033,617 A | 7/1977 | Cocuzza et al. | 203/27 |
| 4,134,797 A | 1/1979 | Ozero | 203/75 |
| 4,257,852 A * | 3/1981 | Worrell | 203/99 |
| 4,966,657 A | 10/1990 | Delannoy et al. | 203/76 |
| 5,529,667 A | 6/1996 | Coffey | 203/96 |

FOREIGN PATENT DOCUMENTS

| | | |
|---|---|---|
| GB | 1180822 | 2/1970 |
| WO | 97/19069 | 3/1997 |

OTHER PUBLICATIONS

*Chem. Ing. Technik.*, 67(12), 1614–1618, 1995.

* cited by examiner

*Primary Examiner*—Virginia Manoharan
(74) *Attorney, Agent, or Firm*—Keil & Weinkauf

(57) ABSTRACT

In a process for purification of ethylene oxide by distillation an aqueous mixture comprising ethylene oxide, formaldehyde and at least 5% by weight of water is introduced via a feed into a distillation apparatus comprising at least one distillation column, the mixture being introduced at a height above the bottom of at least 8 theoretical stages, the ethylene oxide is taken off at the top and in the bottom phase a mixture is obtained which contains less than 5% by weight of ethylene oxide.

6 Claims, 1 Drawing Sheet

PURE ETHYLENE OXIDE DISTILLATION PROCESS

BACKGROUND OF THE INVENTION

The invention relates to processes and an apparatus for the purification of ethylene oxide by distillation.

Pure ethylene oxide is a product manufactured worldwide in amounts of several million tonnes per year. The last process step in the preparation of pure ethylene oxide is purification by distillation, with ethylene oxide being isolated from an aqueous solution.

The critical factor in the purification of ethylene oxide by distillation is that aldehydes, in particular formaldehyde and acetaldehyde, which are present in the feed, do not pass into the pure product. The most important reasons for formaldehyde having to be separated off in the purification of ethylene oxide by distillation are high product purity requirements (frequently below 10 ppm of total aldehyde) and the introduction of novel catalysts which lead to higher concentrations of formaldehyde in the feed.

GB-B 1,180,822 discloses a process for separating off formaldehyde from an ethylene-oxide-containing aqueous mixture. The degree of purity of the pure ethylene oxide achieved in the distillation substantially depends in this process on the amount of fresh water used as scrubbing water. To achieve low formaldehyde contents in the pure oxide, high scrubbing water flow rates must be used, which increases the waste water load. The process is therefore inexpedient.

EP-B 0 322 323 discloses a process for separating off aldehyde impurities from crude ethylene oxide by distillation, in which the crude ethylene oxide is introduced into a column, which has 50 theoretical plates, at the height of the 30th plate from the top. The ethylene oxide is obtained as top product with a content of from about 0.0015 to 0.0020% by weight of aldehyde impurities. The liquid stream exiting at the bottom of the column contains the water present in the crude ethylene oxide and ethylene oxide at 0.15 to 3 times the amount by weight of water—the bottom phase is thus not ethylene-oxide-free, which is a disadvantage in processing terms, since purification by distillation in this case can only be operated economically in conjunction with a glycol plant. The high ethylene oxide content in the bottom phase, in addition, has the consequence that there are only small temperature differences between top and bottom in the column used for purification of ethylene oxide by distillation in the known process.

Because of the disadvantages in the abovementioned processes for purification of ethylene oxide by distillation, process are customarily presently used in which the pure ethylene oxide is obtained as a side stream: U.S. Pat. No. 4,134,797 discloses, for example, a process for purification of ethylene oxide by distillation, in which crude ethylene oxide, which is contaminated with aldehydes such as formaldehyde and acetaldehyde, is purified in a column by means of fractionation or via a plurality of gas-liquid contact stages. The crude ethylene oxide is introduced into the column at a height of preferably from 1 to 20 theoretical gas-liquid contact stages. The pure oxide having a content of generally less than 20 ppm of formaldehyde is obtained as a side stream. The top product obtained is an ethylene-oxide-containing, formaldehyde-enriched stream. The disadvantages of this process are the high expenditure on equipment, the increase in the amount of pure ethylene oxide, which causes safety problems, in the column and the fact that crude oxide is only partially converted into pure oxide (contaminated top product).

It is an object of the present invention, therefore, to provide a process which is simple to perform and at the same time enables a product to be produced, in the purification of ethylene oxide by distillation, which is substantially free of formaldehyde. For the purposes of the invention, substantially free means, for example, that starting from a content of approximately 50 ppm or more in the feed the purified ethylene oxide obtained contains only approximately 4 ppm or less formaldehyde. Furthermore, the process shall also satisfy stringent safety requirements. In addition, it shall lead to an ethylene oxide which is free from formaldehyde to a high degree, without scrubbing steps involving high amounts of waste water.

We have found that this object is achieved according to the invention by a process for the purification of ethylene oxide by distillation, comprising the step in which an aqueous mixture comprising ethylene oxide, formaldehyde and at least 5% by weight of water is introduced via a feed into a distillation apparatus comprising at least one distillation column, the mixture being introduced at a height above the bottom of at least 8, preferably from 12 to 56, theoretical stages, the ethylene oxide is taken off at the top and in the bottom phase a mixture is obtained which contains less than 5% by weight, preferably less than 0.05% by weight, of ethylene oxide.

In addition, to carry out the process according to the invention, an apparatus is provided which comprises a distillation column having a feed (1) at a height above the bottom (4) of at least 8 theoretical stages or, in the case of a plate column, of at least 12 plates above the bottom (4), a top take-off (3), optionally a side take-off (5), and also flame-arresting packings and optionally an intermediate reboiler between feed (1) and bottom (4).

In another embodiment, a process is provided for purification of ethylene oxide by distillation, which process comprises the step in which an aqueous mixture comprising ethylene oxide, formaldehyde and at least 5% by weight of water is introduced via a feed into a distillation apparatus comprising at least one packed column which contains a structured or bulk packing and has a specific mass transfer area A, the mixture being introduced at a height above the bottom of at least $x_{min}$ (in m) which, for a given specific mass transfer area A (in $m^2/m^3$), is given by the equation $$x_{min} = 5.5 \text{ m} - A \cdot 0.006 \text{ m}^2,$$

the ethylene oxide is taken off at the top and in the bottom phase a mixture is obtained which contains less than 5% by weight, preferably less than 0.05% by weight, of ethylene oxide.

In a further embodiment, a process for the purification of ethylene oxide by is distillation is provided, which comprises the step in which an aqueous mixture comprising ethylene oxide, formaldehyde and at least 5% by weight of water is introduced via a feed into a distillation apparatus comprising at least one plate column, the mixture being introduced at a height above the bottom of at least 12, preferably from 16 to 84 plates, the ethylene oxide is taken off at the top and in to the bottom phase a mixture is obtained which contains less than 5% by weight, preferably less than 0.05% by weight, of ethylene oxide.

The crude ethylene oxide fed comprises ethylene oxide, formaldehyde and at least 5% by weight, preferably from 20 to 60% by weight, of water.

In all said embodiments, it is particularly preferred if the process is conducted in such a manner that the bottom mixture contains less than 100 ppm of ethylene oxide ppm, here and elsewhere, are by weight. At such low concentrations of ethylene oxide in the bottom phase of the column—highly predominantly aqueous bottom product—the bottom temperature in the column is far higher than the temperature at the top of the column where there is pure ethylene oxide. In the column, there is then, above the bottom, a spatially narrow region in which the temperature changes sharply.

A feature of the process according to the invention is that the feed into the purification by distillation is markedly above the temperature jump over the bottom in the column. The crude ethylene oxide is introduced according to the invention at a height of at least 8, preferably from 12 to 56, theoretical stages, or at least 12, preferably from 18 to 84, plates over the bottom.

If a packed column, containing structured or bulk packings, is used for the separation, the crude ethylene oxide is introduced at a minimum height $x_{min}$ given by the abovementioned equation as a function of the specific mass transfer area; preferably, the aqueous mixture is introduced via the feed at a height of from 1.5 $x_{min}$ to 7 $x_{min}$. For example, for a specific mass transfer area of 250 $m^2/m^3$, the equation gives a minimum height of 4 m, preferably an introduction height of from 6 to 28 m. In the case of a specific mass transfer area of 500 $m^2/m^3$, this gives a minimum introduction height of 2.5 m, a preferred introduction height of from 3.75 m to 17.5 m. Preferably, the mass sprcific transfer area A is a range from 100 $m^2/m^3$ to 500 $m^2/m^3$.

In the process according to the invention, the crude ethylene oxide can also be introduced via a plurality of feed lines. The lowest of the plurality of feed lines is preferably situated in this case at the abovementioned distance from the bottom according to the invention. The process can also be carried out in such a manner that more than one column is used. The minimum distance according to the invention is then preferably maintained between the crude ethylene oxide feed point or points and the bottom.

In the influent aqueous mixture, the formaldehyde is predominantly present in the form of methylene glycol, which is formed in an equilibrium reaction with water.

By introducing according to the invention the aqueous mixture into the distillation apparatus at a certain, as defined above, (minimum) distance from the bottom, the zone between the feed and the bottom of the column becomes according to the invention so long that monomeric formaldehyde, which is released in the bottom phase as a result of the high temperatures, owing to the equilibrium lying on the side of monomeric formaldehyde at high temperatures, is reabsorbed by the feed stream running in countercurrent.

In addition, in a particularly preferred embodiment of the process according to the invention, it is provided that residues of formaldehyde which, despite the abovedescribed measure, pass into the enrichment part of the column, are scrubbed out by feeding a small stream of water into the enrichment part of the column; ie., that at a height of at least 1 theoretical stage or plate, preferably 3 to 20 theoretical stages or plates, above the feed of the aqueous mixture comprising ethylene oxide, formaldehyde and said minimum amount of water, a further mixture, principally comprising water or essentially water alone, is additionally introduced via a feed line. Feed values of about 0.02 for the ratio mass of water/mass of ascending gas stream are sufficient here. The monomeric formaldehyde released in the bottom phase is preferably absorbed while still in the stripping part of the purification by distillation by the abovementioned further aqueous feed stream. Residues of monomeric formaldehyde which pass into the enrichment part are thus scrubbed out by the added water.

BRIEF DESCRIPTION OF THE DRAWINGS

In the accompanying drawing.

Figure 1:
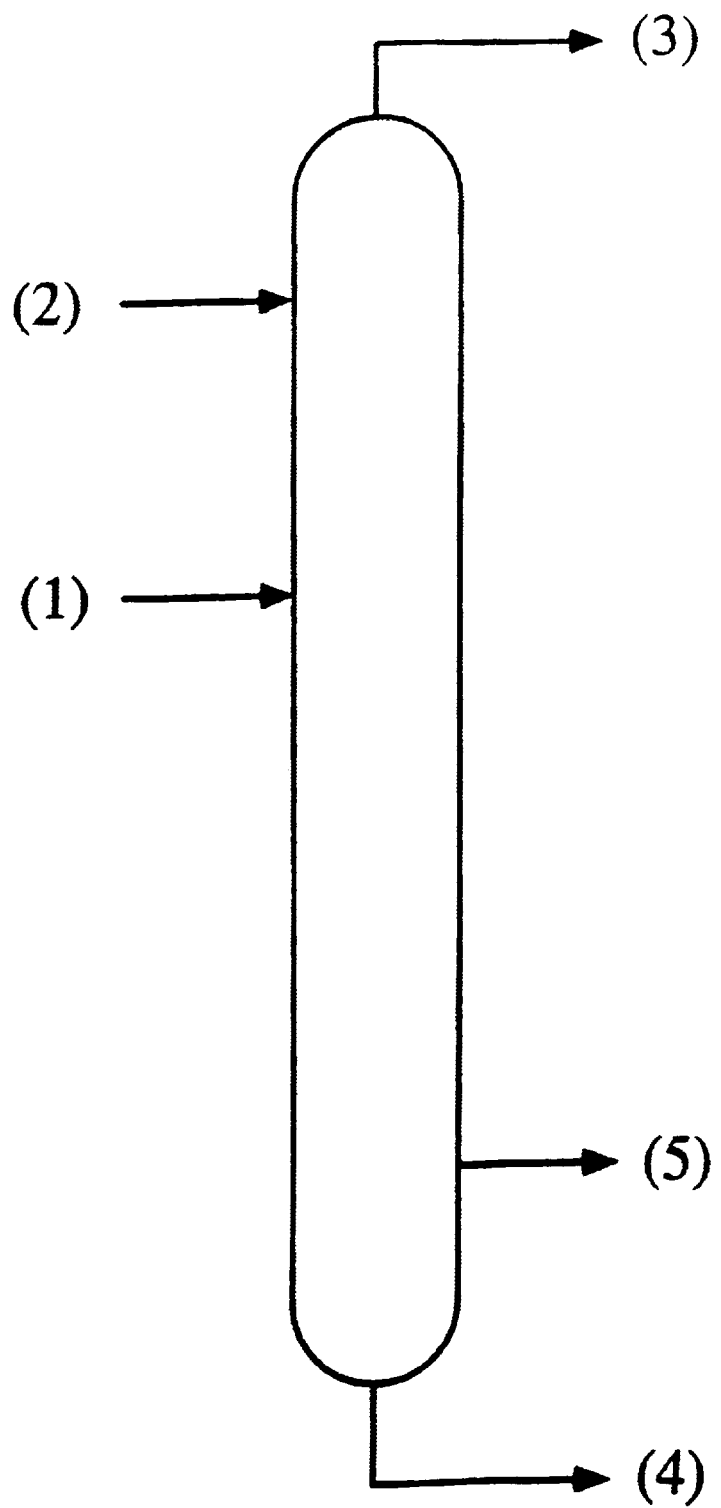
FIG. 1 shows a preferred embodiment of the apparatus used to carry out the process according to the invention.

The FIGURE shows an embodiment in which the process is implemented in a single column. Between the feed (1) point of the crude ethylene oxide, which comprises water, acetaldehyde and formaldehyde, and the bottom phase (4) of water, acetaldehyde and formaldehyde, the minimum distance according to the invention, as explained above, is maintained. In the preferred embodiment according to FIG. 1, the further aqueous mixture, preferably water, which serves to absorb residues of monomeric formaldehyde, is fed at the point marked by (2). The product—pure ethylene oxide—is taken off overhead (3).

In the process according to the invention, a substantially formaldehyde-free product is taken off at the top of the column. Between the feed (1) and the bottom take-off (4), in a particularly preferred embodiment there is a side take-off (5) via which a stream of ethylene oxide, water, acetaldehyde and formaldehyde is taken off which is enriched with acetaldehyde in comparison with the feed. To reduce operating costs, in a further particularly preferred embodiment of the process according to the invention between the feed (1) and the bottom take-off (4) there is provided an intermediate reboiler into which heat is introduced at a lower temperature than in the bottoms reboiler. In addition, in a very particularly preferred embodiment of the process according to the invention, for safety reasons, flame-arresting arranged packings, as are described, for example, in WO 97/19069, are used in the column or at the feeds and/or take-offs to achieve the separation action Typical values for the concentration of formaldehyde in the product are below from 1 to 2 ppm.

DETAILED DESCRIPTION

EXAMPLE

The process according to the invention was investigated by a works test in an ethylene oxide plant [site: Ludwigshafen]. In this test, at formaldehyde concentrations in the feed of about 170 ppm, a formaldehyde concentration in the top product of 2 ppm was achieved.

We claim:

1. A process for purification of ethylene oxide by distillation, comprising the step in which an aqueous mixture comprising ethylene oxide, formaldehyde and at least 5% by weight of water is introduced via a feed into a distillation apparatus comprising at least one packed column which contains a structured or bulk packing and has a specific mass transfer area A, the mixture being introduced at a height above the bottom of at least $x^{min}$, in m, which for a given specific mass transfer area A, in $m^2/m^3$, is given by the equation $$x^{min} = 5.5 \text{ m} - A \cdot 0.006 \text{ m}^2,$$

pure ethylene oxide containing 4 ppm or less formaldehyde, is taken off at the top and in the bottom phase a mixture is obtained which contains less than 5% by weight of ethylene oxide;

an acetaldehyde enriched fraction is removed as a sidestream from the column at a side take-off located between the too and bottom of the column, and wherein the aqueous mixture is introduced via the feed at a height of from 1.5 $x^{min}$ to 7 $x^{min}$.

2. A process as claimed in claim 1, wherein the specific mass transfer area A is in the range from 100 m²/m³ to 500 m²/m³.

3. A process as claimed in claim 2, which further comprises a step in which further mixture, comprising water, is additionally introduced via a feed line at a height of at least one theoretical stage of plate above the feed of the aqueous mixture.

4. A process as claimed in claim 1, which further comprises a step in which further mixture, comprising water, is additionally introduced via a feed line at a height of at least one theoretical stage or plate above the feed of the aqueous mixture.

5. A process for purification of ethylene oxide by distillation, comprising the step in which an aqueous mixture comprising ethylene oxide, formaldehyde and at least 5% by weight of water is introduced via a feed into a distillation apparatus comprising at least one packed column which contains a structured or bulk packing and has a specific mass transfer area A, the mixture being introduced at a height above the bottom of at least $x^{min}$, in m, which, for a given specific mass transfer area A, in m²/m³, is given by the equation $$x^{min} = 5.5 \text{ m} - A \cdot 0.006 \text{ m}^2,$$

pure ethylene oxide containing 4 ppm or less formaldehyde, is taken off at the top and in the bottom phase a mixture is obtained which contains less than 5% by weight of ethylene oxide;

an acetaldehyde enriched fraction is removed as a sidestream from the column at a side take-off located between the top and bottom of the column, and wherein the specific mass transfer area A is in the range from 100 m²/m³ to 500 m²/m³.

6. A process as claimed in claim 5, which further comprises a step in which further mixture, comprising water, is additionally introduced via a feed line at a height of at least one theoretical stage or plate above the feed of the aqueous mixture.

* * * * *